US010602884B2

(12) United States Patent
Gargano

(10) Patent No.: US 10,602,884 B2
(45) Date of Patent: Mar. 31, 2020

(54) MULTI-FUNCTIONAL TOWEL

(71) Applicant: Katlien Gargano, Hauppauge, NY (US)

(72) Inventor: Katlien Gargano, Hauppauge, NY (US)

( * ) Notice: Subject to any disclaimer, the term of this patent is extended or adjusted under 35 U.S.C. 154(b) by 51 days.

(21) Appl. No.: 15/932,020

(22) Filed: Jan. 25, 2018

(65) Prior Publication Data
US 2018/0317718 A1 Nov. 8, 2018

Related U.S. Application Data

(60) Provisional application No. 62/602,775, filed on May 5, 2017.

(51) Int. Cl.
*A47K 10/02* (2006.01)
*B32B 5/06* (2006.01)
*B32B 9/02* (2006.01)
*A01N 59/16* (2006.01)
*B32B 9/04* (2006.01)

(52) U.S. Cl.
CPC ............. *A47K 10/02* (2013.01); *A01N 59/16* (2013.01); *B32B 5/06* (2013.01); *B32B 9/02* (2013.01); *B32B 9/047* (2013.01); *B32B 2250/02* (2013.01); *B32B 2307/728* (2013.01); *B32B 2555/00* (2013.01)

(58) Field of Classification Search
USPC .......................................................... 34/283
See application file for complete search history.

(56) References Cited

U.S. PATENT DOCUMENTS

| 7,634,819 | B2 | 12/2009 | Grey | .................................. 2/207 |
| 8,844,158 | B2 * | 9/2014 | Dehn | ................ A61F 13/00008 156/305 |
| 9,986,742 | B2 * | 6/2018 | Toreki | ..................... D06M 11/44 |
| 2004/0214495 | A1 * | 10/2004 | Foss | ........................ A01N 57/16 442/199 |
| 2005/0198735 | A1 | 9/2005 | Winters | ............................ 5/495 |
| 2006/0083710 | A1 * | 4/2006 | Joerger | .................. A01N 43/16 424/76.1 |
| 2007/0014967 | A1 * | 1/2007 | Tingle | ..................... D03D 15/00 428/96 |

(Continued)

FOREIGN PATENT DOCUMENTS

| CN | 2680178 Y | 2/2005 |
| CN | 2887909 Y | 4/2007 |

(Continued)

*Primary Examiner* — Stephen M Gravini
(74) *Attorney, Agent, or Firm* — Bernard S. Hoffman

(57) ABSTRACT

A multi-functional towel for drying the body of a user and for drying the hair of the user using different parts of the multi-functional towel for each so as to avoid damaging the hair of the user and also inhibiting microbial growth and associated odors during both drying processes. The multi-functional towel includes one layer, an opposing layer, and a microbial growth and associated odors inhibitor. The one layer is for drying the body of the user. The opposing layer opposes the one layer and is for drying the hair of the user. The microbial growth and associated odors inhibitor is impregnated in the one layer and in the opposing layer during manufacturing to avoid formation of microbial growth and associated odors during both drying processes.

20 Claims, 4 Drawing Sheets

(56) References Cited

U.S. PATENT DOCUMENTS

| | | | | |
|---|---|---|---|---|
| 2012/0210594 A1* | 8/2012 | Heyman | ................ | A47K 10/02 34/283 |
| 2016/0165981 A1* | 6/2016 | Dorn | ..................... | A63B 57/00 2/249 |
| 2017/0156340 A1* | 6/2017 | Toreki | .................... | D06M 11/44 |
| 2018/0064615 A1* | 3/2018 | Brahms | ................ | A61K 9/0014 |
| 2018/0317718 A1* | 11/2018 | Gargano | ................ | A47K 10/02 |

FOREIGN PATENT DOCUMENTS

| | | | | |
|---|---|---|---|---|
| CN | 2887912 Y | 4/2007 | | |
| DE | 102008063229 A1 * | 7/2010 | ....... | A61F 13/00008 |
| EP | 2199447 A1 * | 6/2010 | ....... | A61F 13/00008 |
| JP | 3161021 B2 * | 4/2001 | | |
| WO | WO-2010069592 A1 * | 6/2010 | ....... | A61F 13/00008 |

* cited by examiner

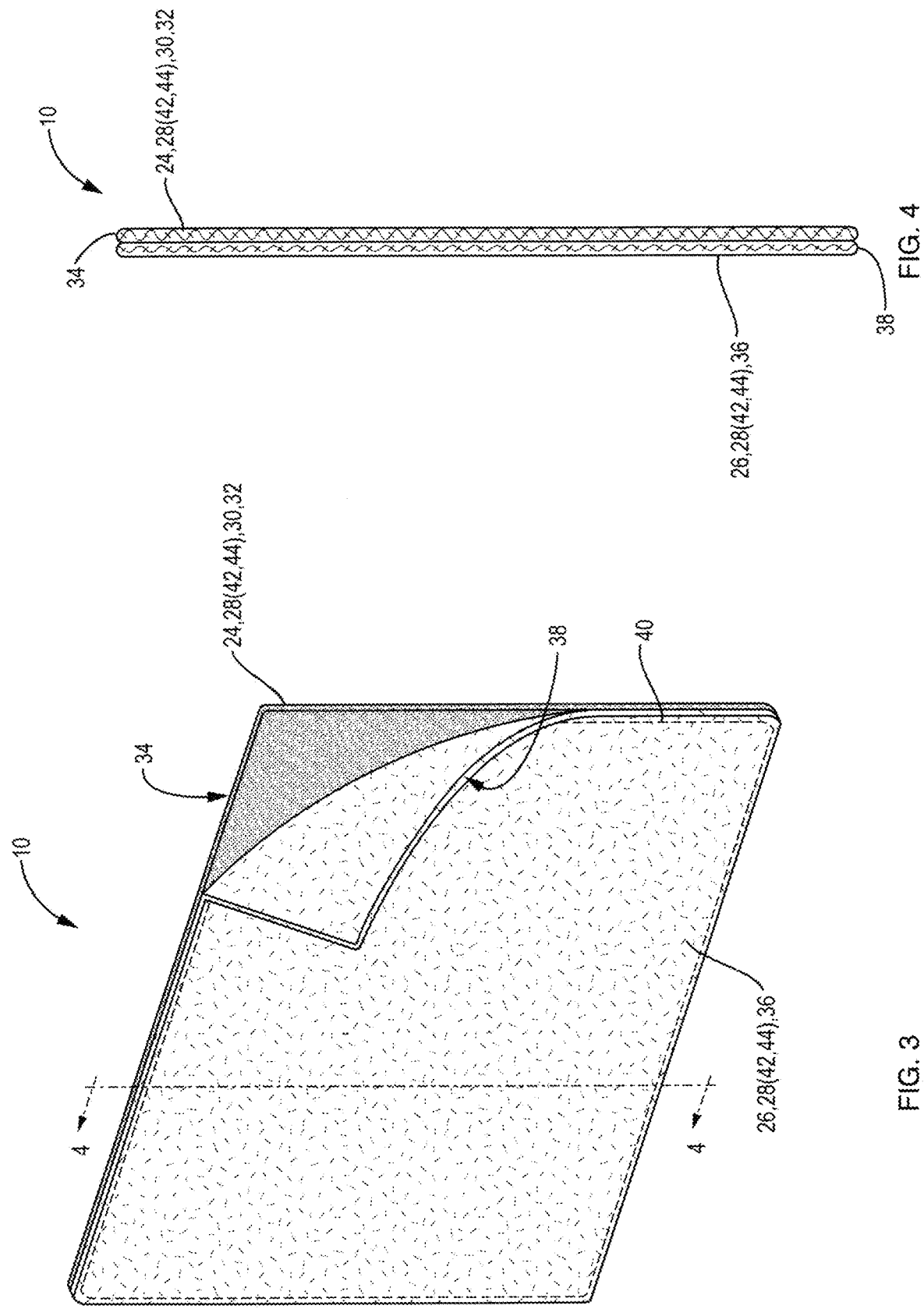

MULTI-FUNCTIONAL TOWEL

BACKGROUND OF THE INVENTION

Field of the Invention

The embodiments of the present invention relate to a towel, and more particularly, the embodiments of the present invention relate to a multi-functional towel for drying the body of a user and for drying the hair of the user using different parts of the multi-functional towel for each so as to avoid damaging the hair of the user and also inhibiting microbial growth and associated odors during both drying processes.

Description of the Prior Art

Numerous innovations for towels have been provided in the prior art, which will be described below in chronological order to show advancement in the art, and which are incorporated herein in their entirety by reference thereto. Even though these innovations may be suitable for the specific individual purposes to which they address, however, they differ from the embodiments of the present invention.

Chinese Patent Number CN 2680178 Y to Wang

Chinese Patent Number CN 2680178 Y—granted to Wang on Feb. 23, 2005 in International class A47K10 and subclass 02—teaches a double-sided towel. One layer of the towel is provided with a plain cloth pane surface and the other layer of the towel is provided with a curl surface. The plain cloth pane surface uses chaine and filling yarn to waver the towel, and the chaine and the filling yarn are in the plain cloth pane state. The curl surface draws the chaine and the filling yarn from the plain cloth surface to get a curl. The curl drew by the curl surface each time is the double curl ring.

Chinese Patent Number CN 2887909 Y to Liu

Chinese Patent Number CN 2887909 Y—granted to Liu on Apr. 11, 2007 in International class A47K10 and subclass 02—teaches a multi-functional towel that applies cotton as well as Terylene. The towel is provided with a base cloth layer in the middle. Both layers of the layer are, respectively, provided with two terry functional layers, one of which is woven from the cotton yarn and the other is woven from the Terylene superfine fibre. Both layers of the towel are, respectively, woven from different yarns.

Chinese Patent Number CN 2887912 Y to Liu

Chinese Patent Number CN 2887912 Y—granted to Liu on Apr. 11, 2007 in International class A47K10 and subclass 02—teaches a multi-functional towel that applies cotton as well as composite silk. The towel is provided with a base cloth layer in the middle, and both layers of the layer are, respectively, provided with a terry functional layer that is woven of cotton yarn, and the other terry functional layer is woven of polyamide fibre, as well as, Terylene superfine composite fibre. Both layers of the towel are, respectively, woven from different yarns.

United States Patent Application Publication Number US 2005/0198735 A1 to Winters United States Patent Application Publication Number US 2005/0198735 A1—published to Winters on Sep. 15, 2005 in U.S. class 5 and subclass 495—teaches a two-sided or reversible terry cloth sheet set. The pillowcases, bed skirt, valance, and drapes are also two-sided or reversible. The sets are made to order in the bed size of choice. The set comes with a two layered (one layer is terry cloth and the other is cotton) or a reversible fitted sheet, a two layered (one layer is terrycloth and the other is cotton) or a reversible flat sheet, one twin set or two full, queen, king sets, and pillowcases that are also two-sided or reversible.

U.S. Pat. No. 7,634,819 B2 to Grey

U.S. Pat. No. 7,634,819 B2—issued to Grey on Dec. 22, 2009 in U.S. class 2 and subclass 207—teaches a head wrap or scarf in a single layer having a first layer that is more slippery against another surface and a second layer that is rougher and less slippery than the first layer. The single layer is formed of two fibers of two different materials, with a greater proportion of a first slippery fabric toward the first layer of the head wrap and a greater proportion of rougher fabric toward the second layer of the head wrap.

It is apparent that numerous innovations for towels have been provided in the prior art that are adapted to be used. Furthermore, even though these innovations may be suitable for the specific individual purposes to which they address, however, they would not be suitable for the purposes of the embodiments of the present invention as heretofore described.

SUMMARY OF THE INVENTION

Thus, an object of the embodiments of the present invention is to provide a multi-functional towel for drying the body of a user and for drying the hair of the user using different parts of the multi-functional towel for each so as to avoid damaging the hair of the user and also inhibiting microbial growth and associated odors during both drying processes, which avoids the disadvantages of the prior art.

Briefly stated, another object of the embodiments of the present invention is to provide a multi-functional towel for drying the body of a user and for drying the hair of the user using different parts of the multi-functional towel for each so as to avoid damaging the hair of the user and also inhibiting microbial growth and associated odors during both drying processes. The multifunctional towel includes one layer, an opposing layer, and a microbial growth and associated odors inhibitor. The one layer is for drying the body of the user. The opposing layer opposes the one layer and is for drying the hair of the user while avoiding damaging the hair of the user. The microbial growth and associated odors inhibitor is impregnated in the one layer and in the opposing layer during manufacturing to avoid formation of microbial growth and associated odors during both drying processes.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying figures of the drawing.

BRIEF DESCRIPTION OF THE FIGURES OF THE DRAWING

The figures of the drawing are briefly described as follows:

FIG. 3 is an enlarged diagrammatic perspective view of the multi-functional towel of the embodiments of the present invention identified by ARROW 3 in FIGS. 1 and 2;

FIG. 4 is a diagrammatic cross sectional view taken along LINE 4-4 in FIG. 3;

LIST OF REFERENCE NUMERALS UTILIZED IN THE FIGURES OF THE DRAWING

Introductory

Figure 1:
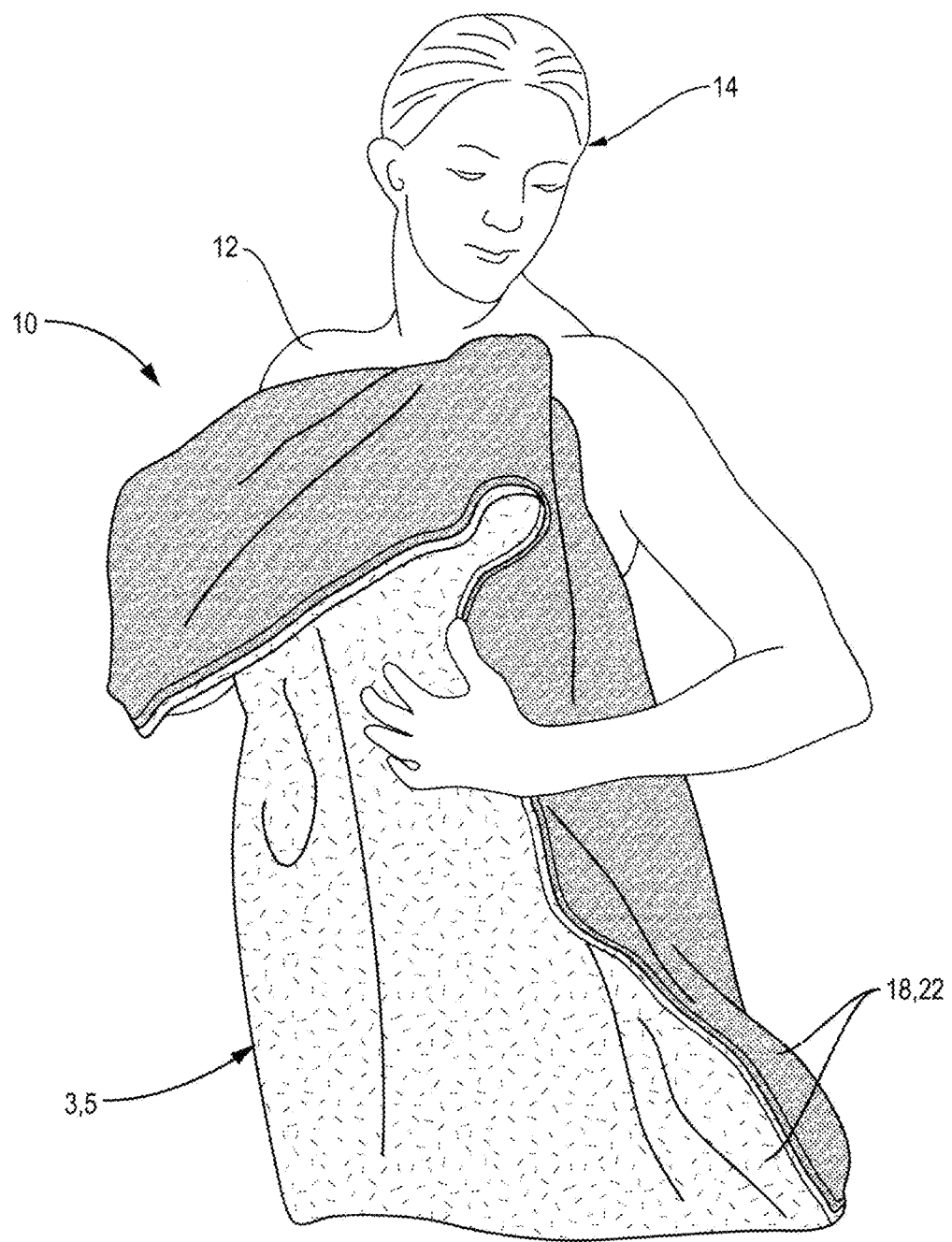
FIG. 1 is a diagrammatic perspective view of the multi-functional towel of the embodiments of the present invention drying the body of a user and inhibiting microbial growth and associated odors during the drying process.

10 multi-functional towel of embodiments of present invention for drying body 12 of user 14 and for drying hair 16 of user 14 using different parts 18 of multi-functional towel 10 for each so as to avoid damaging hair 16 of user 14 and to also inhibit microbial growth 20 and associated odors 22 during both drying processes
12 body of user 14
14 user
16 hair of user 14
18 different parts of multi-functional towel 10
20 microbial growth
22 odors associated with microbial growth

Overall Configuration of Multi-Functional Towel 10, Specific Configuration of One Layer 24, Specific Configuration of Opposing Layer 26, and Specific Configuration of Microbial Growth and Associated Odors Inhibiter 28

Overall Configuration of Multi-Functional Towel 10

24 one layer for drying body 12 of user 14
26 opposing layer for drying hair 16 of user 14 while avoiding damaging, such as, by depilation 18, hair 16 of user 14
28 microbial growth and associated odors inhibitor

Specific Configuration of One Layer 24

30 terrycloth of one layer 24 for maximizing absorbency 32 when drying body 12
32 absorbency
34 perimeter of one layer 18

Specific Configuration of Opposing Layer 26

36 cotton of opposing layer 20 for minimizing depilation 18 when drying hair 16
38 perimeter of opposing layer 18
40 stitches

Specific Configuration of Microbial Growth and Associated Odors Inhibiter 28

42 silver ion of microbial growth and associated odors inhibiter 28
44 compounds made from silver ion 42

Specific Configuration of Alternate Embodiment of Multi-Functional Towel 110

146 binding

DETAILED DESCRIPTION OF THE PREFERRED EMBODIMENTS OF THE PRESENT INVENTION

Introductory

Figure 2:
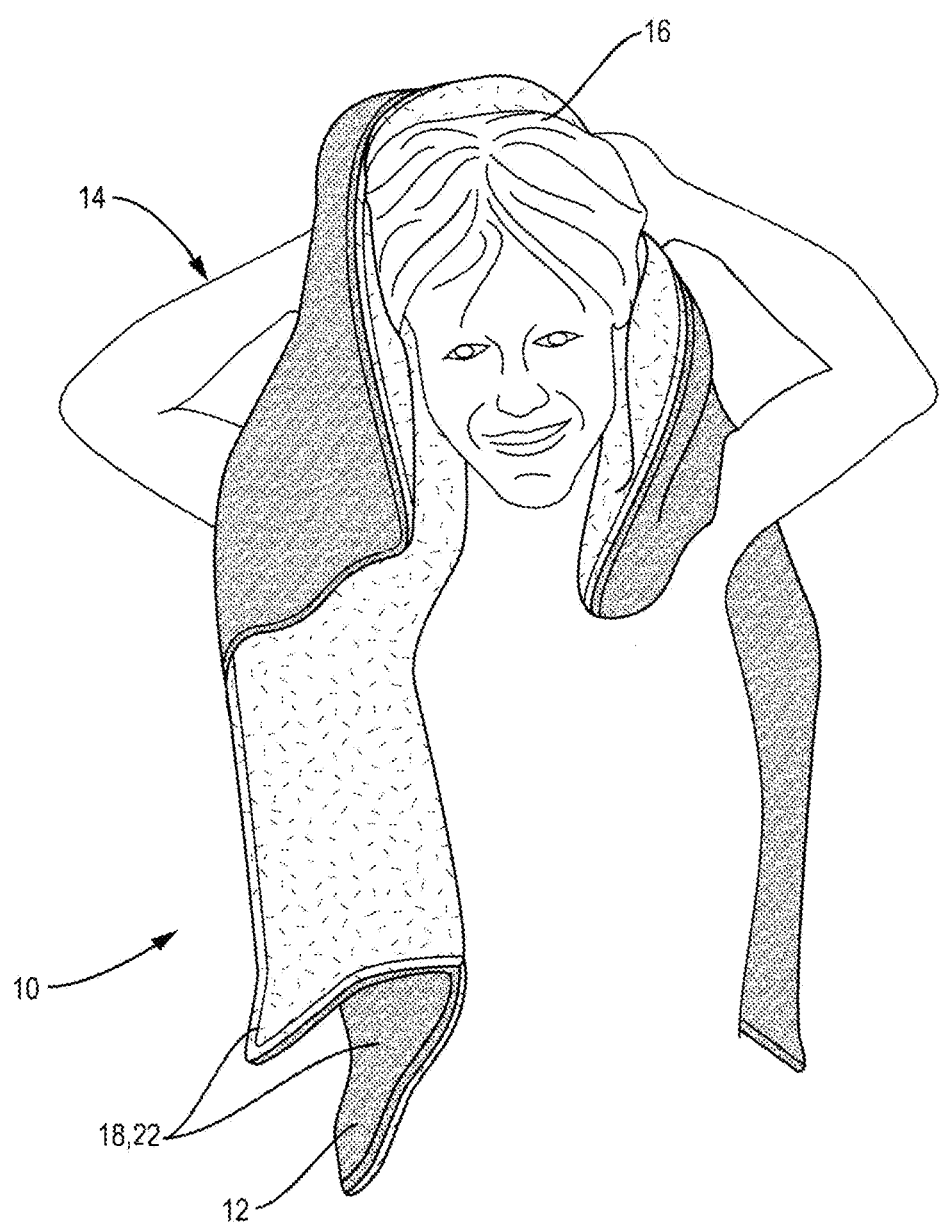
FIG. 2 is a diagrammatic perspective view of the multi-functional towel of the embodiments of the present invention drying the hair of a user and also inhibiting microbial growth and associated odors during the drying process.

Referring now to the figures, in which like numerals indicate like parts, and particularly to FIGS. 1 and 2, the multi-functional towel of the embodiments of the present invention is shown generally at 10 for drying the body 12 of a user 14 (FIG. 1) and for drying the hair 16 of the user 14 (FIG. 2) using different parts 18 of the multi-functional towel 10 for each so as to avoid damaging the hair 16 of the user 14 and to also inhibit microbial growth 20 and associated odors 22 during both drying processes.

The Overall Configuration of the Multi-Functional Towel 10, the Specific Configuration of the One Layer 24, the Specific Configuration of the Opposing Layer 26, and the Specific Configuration of the Microbial Growth and Associated Odors Inhibitor 28

The overall configuration of the multi-functional towel 10, the specific configuration of the one layer 24, the specific configuration of the opposing layer 26, and the specific configuration of the microbial growth and associated odors inhibitor 28 can best be seen in FIGS. 3 and 4, and as such, will be discussed with reference thereto.

The Overall Configuration of the Multi-Functional Towel 10

The multi-functional-towel 10 comprises one layer 24, an opposing layer 26, and a microbial growth and associated odors inhibitor 28. The one layer 24 is for drying the body 12 of the user 14. The opposing layer 20 opposes the one layer 18 and is for drying the hair 16 of the user 14 while avoiding damaging, such as, by depilation 18, the hair 16 of the user 14. The microbial growth and associated odors inhibitor 28 is impregnated in the one layer 24 and in the opposing layer 26 during manufacturing.

The Specific Configuration of the One Layer 24

The one layer 24 is made of terrycloth 30 for maximizing absorbency 32 when drying the body 12.

The one layer 18 is generally rectangular-shaped defined by a perimeter 34.

The Specific Configuration of the Opposing Layer 26

The opposing layer 20 is made of cotton 36 for minimizing depilation 18 when drying the hair 16.

The opposing layer 18 is generally rectangular-shaped defined by a perimeter 38. The presence of the multi-functional towel 10, i.e., the double-sided towel, allows for application of the moisture wicking effect without damaging the cotton 36, which functions as a protective barrier between the hair 16 and the multi-functional towel 10.

The opposing layer 18 is attached to the one layer 24 by only the perimeter 34 of the one layer 18 being attached to only the perimeter 38 of the opposing layer 18, respectively.

Figure 5:
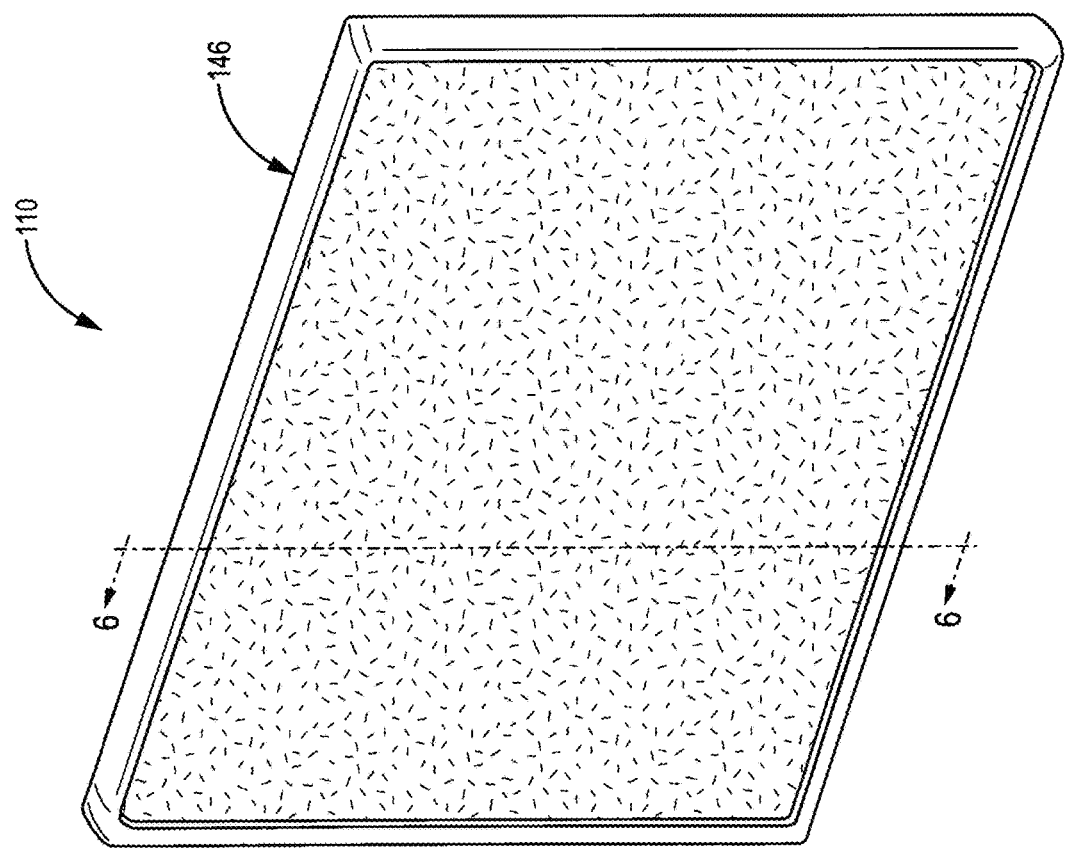
FIG. 5 is an enlarged diagrammatic perspective view of an alternate embodiment of the multi-functional towel identified by ARROW 5 in FIGS. 1 and 2 and having a peripheral binding therearound.

The perimeter 34 of the one layer 18 is attached to the perimeter 38 of the opposing layer 18, preferably, by stitches 40 so as to allow the one layer 18 and the opposing layer 20 to selectively separate from each other than at the perimeter 34 of the first layer 18 and the perimeter 38 of the opposing layer 20 to enhance absorbency (FIG. 5).

The Specific Configuration of the Microbial Growth and Associated Odors Inhibiter 28

The microbial growth and associated odors inhibiter 28 is a silver ion 42 or compound 44 made therefrom.

The Specific Configuration of the Alternate Embodiment of the Multi-Functional Towel 110

Figure 6:
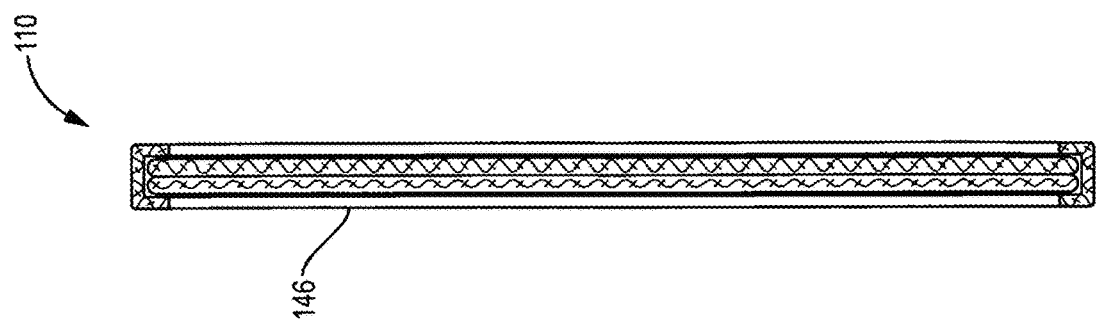
FIG. 6 is a diagrammatic cross sectional view taken along LINE 6-6 in FIG. 5.

The specific configuration of the alternate embodiment of the multi-functional towel 110 can best be seen in FIGS. 5 and 6, and as such, will be discussed with reference thereto.

The multi-functional towel 110 is similar to the multi-functional towel 10, but with the addition of a binding 146.

The binding 146 encloses the perimeter 34 of the one layer 18 and the perimeter 38 of the opposing layer 20, to thereby cosmetically conceal the perimeter 34 of the one layer 18 and the perimeter 38 of the opposing layer 20.

Impressions

It will be understood that each of the elements described above or two or more together may also find a useful application in other types of constructions differing from the types described above.

While the embodiments of the present invention have been illustrated and described as embodied in a multi-functional towel for drying the body of a user and for drying the hair of the user using different parts of the multi-functional towel for each so as to avoid damaging the hair of the user and also to inhibit microbial growth and associated odors during both drying processes, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A multi-functional towel for drying a body of a user and for drying hair of the user using different parts of said multi-functional towel for each so as to avoid damaging the hair of the user and also inhibiting microbial growth and associated odors during both drying processes, comprising:
   a) one layer;
   b) an opposing layer; and
   c) a microbial growth and associated odors inhibitor;
   wherein said one layer is for drying the body of the user;
   wherein said opposing layer opposes said one layer;
   wherein said opposing layer is for drying the hair of the user while avoiding damaging the hair of the user; and
   wherein said microbial growth and associated odors inhibitor is impregnated in said one layer and in said opposing layer during manufacturing to avoid formation of microbial growth and associated odors during both drying processes.

2. The multi-functional towel of claim 1, wherein said one layer is made of terrycloth for maximizing absorbency when drying the body of the user.

3. The multi-functional towel of claim 1, wherein said one layer is generally rectangular-shaped defined by a perimeter.

4. The multi-functional towel of claim 1, wherein said opposing layer is made of cotton for minimizing depilation when drying the hair of the user.

5. The multi-functional towel of claim 3, wherein said opposing layer is generally rectangular-shaped defined by a perimeter.

6. The multi-functional towel of claim 5, wherein said opposing layer is attached to said one layer by only said perimeter of said one layer being attached to only said perimeter of said opposing layer, respectively.

7. The multi-functional towel of claim 5, wherein said perimeter of said one layer is attached to said perimeter of said opposing layer so as to allow said one layer and said opposing layer to selectively separate from each other within said perimeters to enhance absorbency.

8. The multi-functional towel of claim 5, wherein said perimeter of said one layer is attached to said perimeter of said opposing layer by stitches.

9. The multi-functional towel of claim 1, wherein said microbial growth and associated odors inhibiter is a silver ion or a compound made therefrom.

10. The multi-functional towel of claim 5, further comprising binding; and wherein said binding encloses said perimeter of said one layer and said perimeter of said opposing layer, to thereby conceal said perimeter of said one layer and said perimeter of said opposing layer.

11. A method of drying a body and hair of a user, comprising the step of:
   drying the body and the hair of the user with a multi-functional towel, which comprises:
   a) one layer;
   b) an opposing layer; and
   c) a microbial growth and associated odors inhibitor;
   wherein said one layer is for drying the body of the user;
   wherein said opposing layer opposes said one layer;
   wherein said opposing layer is for drying the hair of the user while avoiding damaging the hair of the user; and
   wherein said microbial growth and associated odors inhibitor is impregnated in said one layer and in said opposing layer during manufacturing to avoid formation of microbial growth microbial growth and associated odors during both drying processes.

12. The method of claim 11, wherein said one layer is made of terrycloth for maximizing absorbency when drying the body of the user.

13. The method of claim 11, wherein said one layer is generally rectangular-shaped defined by a perimeter.

14. The method of claim 11, wherein said opposing layer is made of cotton for minimizing depilation when drying the hair of the user.

15. The method of claim 13, wherein said opposing layer is generally rectangular-shaped defined by a perimeter.

16. The method of claim 15, wherein said opposing layer is attached to said one layer by only said perimeter of said one layer being attached to only said perimeter of said opposing layer.

17. The method of claim 15, wherein said perimeter of said one layer is attached to said perimeter of said opposing layer so as to allow said one layer and said opposing layer to selectively separate from each other within said perimeters to enhance absorbency.

18. The method of claim 15, wherein said perimeter of said one layer is attached to said perimeter of said opposing layer by stitches.

19. The method of claim 15, wherein said microbial growth and associated odors inhibiter is a silver ion or a compound made therefrom.

20. The method of claim 19, further comprising binding; and wherein said binding encloses said perimeter of said one layer and said perimeter of said opposing layer, to thereby conceal said perimeter of said one layer and said perimeter of said opposing layer.

* * * * *